United States Patent [19]

Hök et al.

[11] 4,261,208

[45] Apr. 14, 1981

[54] PRESSURE TRANSDUCER

[75] Inventors: Bertil Hök, Upsala; Kenth Nilsson, Akersberga; Gandino Gandini, Solna, all of Sweden

[73] Assignee: Siemens Aktiengesellschaft, Berlin & Munich, Fed. Rep. of Germany

[21] Appl. No.: 11,864

[22] Filed: Feb. 13, 1979

[30] Foreign Application Priority Data

Mar. 17, 1978 [DE] Fed. Rep. of Germany ....... 2811859

[51] Int. Cl.³ ................................................ G01L 9/02
[52] U.S. Cl. .................................... 73/753; 128/673; 128/675; 338/38
[58] Field of Search .................. 73/753, 733; 128/673, 128/674, 675, 723; 338/36, 38, 86

[56] References Cited

U.S. PATENT DOCUMENTS

| | | | |
|---|---|---|---|
| 2,769,070 | 9/1979 | Donald | 338/38 |
| 3,911,902 | 10/1975 | Delpy | 128/675 |
| 3,942,382 | 3/1976 | Hök | 73/753 |

Primary Examiner—Donald O. Woodiel
Attorney, Agent, or Firm—Hill, Van Santen, Steadman, Chiara & Simpson

[57] ABSTRACT

In an exemplary embodiment, the liquid pressure to be measured is in a liquid container with an inner tube forming a measuring cell arranged in an outer tube, which measuring cell can be filled in part with a liquid and in the remainder with a gas. A conduit that can be filled with the liquid leads away from the measuring cell, which conduit is open on its end facing away from the measuring cell and can be directly connected with the fluid in the liquid container. A transducer for generating an electric magnitude which corresponds to the gas volume in the measuring cell is arranged in the measuring cell. A channel is left free between the outer tube and the inner tube for the passage of the fluid. The inner tube is closed on its end facing away from the measuring end of the pressure transducer.

9 Claims, 2 Drawing Figures

PRESSURE TRANSDUCER

BACKGROUND OF THE INVENTION

The invention relates to a pressure transducer for generating an electric signal that corresponds to a liquid pressure to be measured in a liquid container, with a measuring cell arranged in an external tube, which measuring cell can be partly filled with a liquid and the remainder with a gas, in which a line that can be filled up with the liquid leads away from the measuring cell, which line is open at the end facing away from the measuring cell and can be directly connected with the liquid in the liquid container; and in which means for generating an electric magnitude which corresponds to the gas volume in the measuring cell is arranged, as well as with an inner tube enclosed by an outer tube.

A pressure transducer of this type, which is a miniature pressure transducer, is known from the U.S. Pat. No. 3,942,382. In this pressure transducer, a thin capillary extends axially into the measuring cell and connects the inner tube, which serves for the supply of the transmission of fluid, with the line that can be filled with this fluid, which line can be directly connected to the liquid container, for example, a blood vessel. When the transducer is filled with transmission fluid, for example, with salt solution, then this fluid flows via the inner tube through the capillary and into the line which can be directly connected to the liquid container. Upon filling the pressure transducer with the transmission fluid, a meniscus between this fluid and the gas volume at the end of the capillary is supposed to be formed between the inner wall of the outer tube and the outer wall of the capillary. This meniscus must have a specific position in the measuring cell, so that impeccable measuring results can be attained. When the capillary which is supposed to extend axially into the measuring cell lying in the outer tube is somewhat bent or does not lie exactly axially, falsified measurement values can ensue. Because of the capillary, further, the pressure transducer is complicated in its construction.

SUMMARY OF THE INVENTION

The object of the invention is to create a pressure transducer of the type initially cited, whose construction is very simple and in which the position of the meniscus can be dependably fixed.

This object is inventively achieved in that a channel between the outer and inner tube is left free for the passage of the fluid, in that the inner tube is closed at that end facing away from the measuring end of the pressure transducer, and in that the measuring cell is formed by the inner tube. Because of the fact that no capillary axially protrudes through the measuring cell, the position of the meniscus can be easily fixed from the open, outer end of the measuring cell. Because of the fact that the pressure transducer is constructed of few parts, it is very simple in its construction.

A process for filling the pressure transducer inventively consists of the fact that a fluid pump is attached to the end facing away from the measuring end and the measuring cell is filled with a gas which consists of at least two components and that at least one of the components dissolves well in the fluid. Thereby, it is attained that the position of the meniscus in the measuring cell can be fixed dependent on the gas composition.

Further details of the invention derive from the subclaims.

In the following, the invention is explained in greater detail on the basis of an exemplary embodiment illustrated in the accompanying sheet of drawings serving for blood pressure measurement.

DETAILED DESCRIPTION

Figure 1:
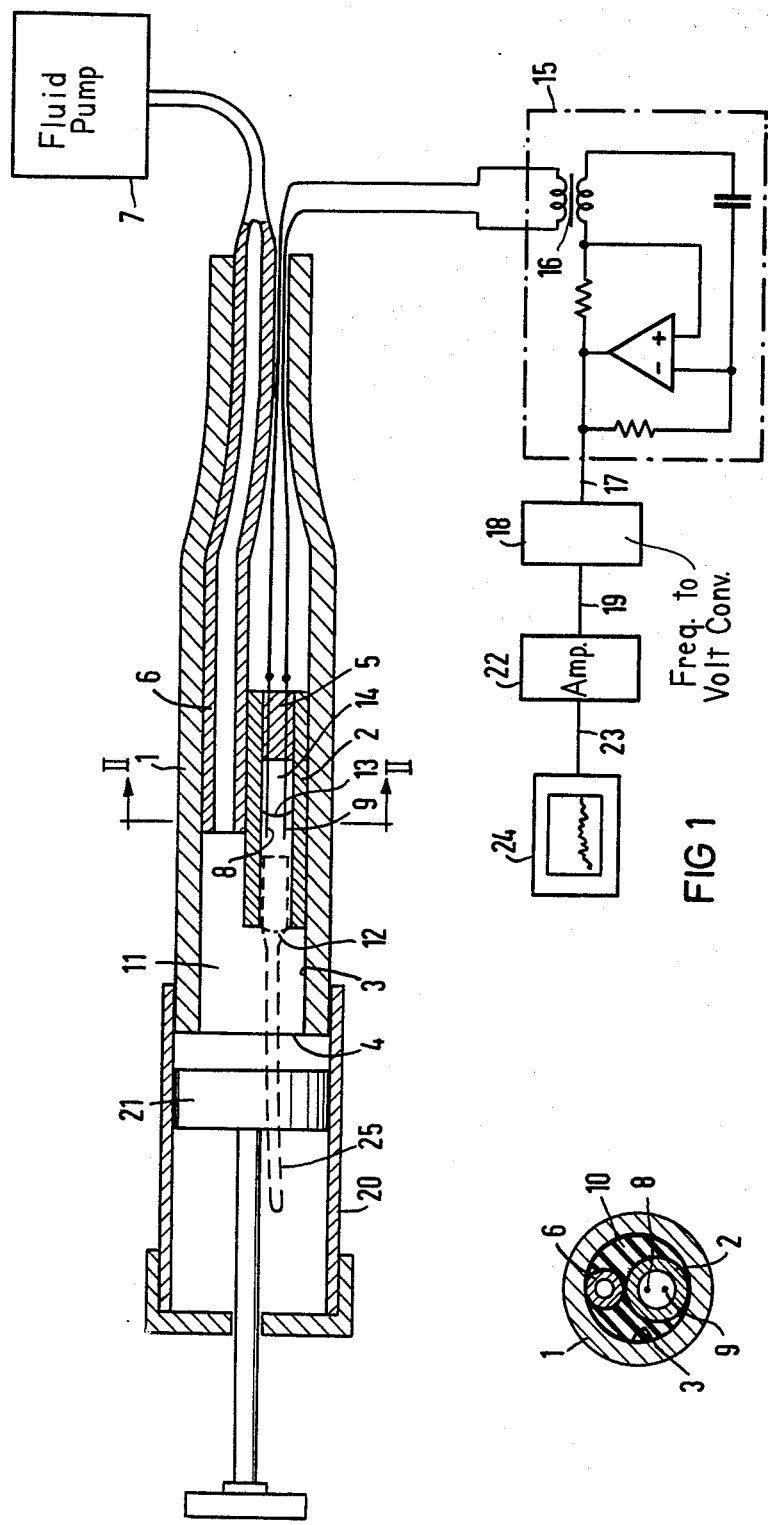
FIG. 1 is a composite diagram including a longitudinal section through an inventive pressure transducer, and including a showing of an exemplary associated electric circuit.

FIG. 1 shows that the pressure transducer, which is a miniature pressure transducer, exhibits an outer tube 1 as well as an inner tube 2 that is enclosed by the outer tube, which inner tube 2 forms the measuring cell. The measuring cell 2 is arranged eccentrically in the outer tube 1 and is fastened to its inner wall 3. The measuring cell 2 is closed at its end 5 facing away from the measuring end 4 of the outer tube 1 or of the pressure transducer, respectively. Moreover, the measuring cell 2 terminates at an interval from the measuring end 4 of the outer tube 1. Between the outer tube 1 and the measuring cell 2, a gap for a fluid line or channel 6 is left free, which fluid line is connected to a fluid pump 7 with salt solution. The fluid pump 7 can be a receptacle in which the salt solution stands under a specific pressure. The fluid resistance, i.e. the diameter, of the fluid line 6 is adapted to the desired fluid flow. In the measuring cell 2, two electrodes 8, 9 made of platinum are arranged at an interval from one another and extend in the longitudinal direction of the tube, which electrodes are attached to a circuit arrangement for measuring the respective resistance between them, which circuit arrangement is to be described in detail later.

Figure 2:
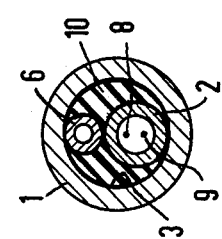
FIG. 2 is a cross section through the pressure transducer according to FIG. 1 along the line II—II.

In FIG. 2, it is shown that the measuring cell 2 and the fluid line 6 are embedded in silicone rubber 10.

When a blood pressure measurement is to be undertaken, the pressure transducer conduit or chamber 11 must be filled with salt solution by means of pump 7 before the pressure transducer can be coupled to the measuring area, for example, in a blood vessel. Salt solution flows from the fluid pump 7 via the fluid line or channel 6 into the space or conduit 11 (which is clear of silicone rubber 10) and presses the air present in the conduit 11 out into the atmosphere. Because of the small dimensions of the pressure transducer, the salt solution dependent on the pressure of the fluid pump, does not flow out into the atmosphere, but rather fills up the space or conduit 11 in the outer tube 1. Because of the construction and position of the measuring cell 2, the air in it is at first not removed. A meniscus 12 is formed exactly at the free end of the measuring cell 2, as is shown by the dot-dash line.

In order to be able to undertake a pressure measurement, the meniscus 12, i.e. the salt solution, must be introduced into the measuring cell 2, so that the free ends of the electrodes 8, 9 are immersed in the salt solution. The meniscus 12 must have a defined position in the measuring cell 2. In FIG. 1, the meniscus which has been pushed into the measuring cell 2 is indicated at 13.

So that an exact fixing of the position of the meniscus is possible, the measuring cell 2 can be filled with a gas mixture of $CO_2$ and air before the pressure transducer conduit 11 is filled with the salt solution. When the pressure transducer conduit 11 is subsequently filled with salt solution, because of the solution of the $CO_2$ of this gas mixture in the salt solution, the salt solution is sucked into the measuring cell 2, and, indeed, up to a level that depends on the composition of the gas mixture. By means of this composition therefore, the position of the meniscus in the measuring cell 2 can be fixed.

For a blood pressure measurement, the pressure transducer is introduced in a blood vessel of a patient, whereby the gas volume 14 enclosed in the measuring cell 2 changes. The respective gas volume corresponds to the pressure of the salt solution and, thus, to the pressure to be measured and is transduced into an electric signal via the electrodes 8, 9.

The resistance between the electrodes 8, 9 is dependent on the position of the meniscus 13 which limits the air volume 14. This resistance influences the frequency of an oscillator 15. Upon connecting the pressure transducer, for example the electrodes 8, 9, with the secondary winding of a transformer 16 of the oscillator 15, a complete galvanic insulation between the pressure transducer and the oscillator 15 is obtained, which is desirable for reasons of safety. An oscillator of this type is described, for example, in the reference "Operational Amplifiers," Page 370, McGraw-Hill, New York, 1971. The oscillator 15 is connected via the line 17 with a device 18 for transforming the frequency into a corresponding voltage. The device 18 in turn is connected via the connection 19 with an amplifier 22 for amplifying the signals from device 18. The amplifier 22 is itself connected via the connection 23 with a recording device 24 for recording the measurement results.

The dimensions of the pressure transducer can be kept very small. In a sample embodiment, the outer diameter was 0.9 mm and the length 4 mm.

For fixing the position of the meniscus in the measuring cell 2, the measuring end 4 of the pressure transducer filled with salt solution can also, for example, be connected to a suction pressure source 20, for example, to a syringe. The suction pressure is determined by means of the change in volume of the space in front of the plunger 21 of the syringe 20, depending upon the pulling back of the plunger 21. Thereby, a part of the air will leave the measuring cell 2 in the form of air bubbles in the salt solution. When the syringe 20 is removed from the pressure transducer, i.e. when the atmospheric pressure is again present at the measuring end 4, a column of salt solution is formed in the measuring cell 2, whose length depends on the amount of gas sucked off out of the measuring cell 2.

By heating a pressure transducer filled with salt solution to a specific temperature, an air expansion in the measuring cell can be attained, so that air in the form of bubbles likewise leaves the measuring cell 2, whereby a desired length of the salt solution column in the measuring cell 2 is formed upon returning to the initial temperature.

A further possibility to determine the length of the salt solution column or the position of the meniscus 13, respectively, is that a rod 25 is introduced into the measuring cell 2 to a depth corresponding to the desired gas volume in a pressure transducer filled with air. When the pressure transducer is filled with salt solution, the rod 25 is again pulled out from the measuring cell 2 and a corresponding salt solution column forms in the measuring cell 2.

It will be apparent that many modifications and variations may be effected without departing from the scope of the novel concepts and teachings of the present invention.

We claim as our invention:

1. A pressure transducer for generating an electric signal which corresponds to a liquid pressure to be measured in a liquid-containing vessel, said transducer comprising a measuring assembly including an outer tube (1) having an internal liquid chamber (11) therein and an inner tube (2) encompassed by the outer tube and providing a measuring cell comprising a measuring fluid conduit which can be filled in part with a liquid and in the remainder with a gas, said measuring fluid conduit within the measuring cell having a measuring end in liquid flow communication with said liquid chamber (11) so that the measuring fluid conduit can be filled with a measuring liquid through said measuring end via the liquid chamber (11), a measuring liquid in said measuring fluid conduit being in direct liquid flow connection with the measuring liquid in said liquid chamber (11) during a measurement operation, said outer tube having means (4) providing an opening to the exterior of said outer tube so that the measuring liquid in said liquid chamber (11) is directly connectable with the liquid in a liquid-containing vessel whose liquid pressure is to be measured, and sensing means coupled with said measuring cell for generating a signal magnitude which corresponds to the gas volume in said measuring fluid conduit of said inner tube (2), means (6) providing a liquid-flow channel between the outer tube (1) and the inner tube (2) for the supply of the measuring liquid to said liquid chamber (11) from the exterior of said outer tube, said inner tube (2) having means (5) for closing the end of said measuring fluid conduit opposite said measuring end thereof, and said measuring assembly having means (e.g. 7) providing for the supply of said measurement liquid to said liquid chamber (11) via said means (6) providing said channel between the outer tube and the inner tube so as to establish a meniscus which is directly coupled with the liquid of the liquid-containing vessel at the exterior of said outer tube (1) via the exterior opening of said outer tube, without any interposition of any solid material and so that the coupling path between the liquid of the liquid-containing vessel and the meniscus is a function only
    of the measuring liquid and is not dependent upon the resilience or deflectability of any interposed solid material.

2. A pressure transducer according to claim 1, characterized in said sensing means comprising two electrodes (8, 9) arranged in spaced relation to each other in the inner tube (2) and extending in the longitudinal direction of the tube, and a circuit arrangement for measuring the resistance between said electrodes.

3. A pressure transducer according to claim 1, characterized in that the inner tube (2) is arranged eccentric in the outer tube (1).

4. A pressure transducer according to claim 1, characterized in that the inner tube (2) ends at an interval from the interior opening (4) of the outer tube (1).

5. A process for filling the pressure transducer according to claim 1, characterized in that a fluid pump (7) supplies measurement liquid to the liquid chamber (11) via the channel between the outer tube and the inner tube, and in the direction toward the exterior opening (4) of the outer tube (1).

6. A process for filling the pressure transducer according to claim 5, characterized in that the measuring cell (2) is filled with a gas that consists of at least two components and in that at least one of the components dissolves well in the measurement liquid.

7. A process for filling the pressure transducer according to claim 5, characterized in that the gas is a mixture of air and $CO_2$.

8. A process for filling the pressure transducer according to claim 5, characterized in that the pressure transducer is heated for the expansion of the air in the measuring cell (2).

9. A process for filling the pressure transducer according to claim 5, characterized in that a bar (25) is introduced into the measuring cell (2) to a depth corresponding to the desired gas volume and is subsequently drawn out again.

* * * * *